United States Patent [19]

Kato et al.

[11] 4,205,074

[45] May 27, 1980

[54] ANTI-SPASMODIC SUBSTITUTED QUINOLIZIDINE AND INDOLIZIDINE COMPOUNDS

[75] Inventors: Hideo Kato; Eiichi Koshinaka, both of Katsuyamashi, Japan

[73] Assignee: Hokuriku Pharmaceutical Co., Ltd., Japan

[21] Appl. No.: 16,515

[22] Filed: Mar. 1, 1979

Related U.S. Application Data

[63] Continuation-in-part of Ser. No. 904,498, May 10, 1978, abandoned, and a continuation-in-part of Ser. No. 904,530, May 10, 1978, abandoned, and a continuation-in-part of Ser. No. 904,533, May 10, 1978, abandoned, and a continuation-in-part of Ser. No. 904,534, May 10, 1978, abandoned, and a continuation-in-part of Ser. No. 904,535, May 10, 1978, abandoned, and a continuation-in-part of Ser. No. 969,400, Dec. 14, 1978, abandoned, and a continuation-in-part of Ser. No. 969,401, Dec. 14, 1978, abandoned.

[30] Foreign Application Priority Data

| | | |
|---|---|---|
| May 16, 1977 [JP] | Japan | 52/55266 |
| Aug. 9, 1977 [JP] | Japan | 52/107270 |
| Nov. 9, 1977 [JP] | Japan | 52/133526 |
| Dec. 8, 1977 [JP] | Japan | 52/146613 |
| Dec. 21, 1977 [JP] | Japan | 52/152841 |
| Feb. 28, 1978 [JP] | Japan | 53/21534 |
| Mar. 22, 1978 [JP] | Japan | 53/31652 |
| Mar. 22, 1978 [JP] | Japan | 53/31653 |
| May 23, 1978 [JP] | Japan | 53/60654 |
| May 23, 1978 [JP] | Japan | 53/60656 |

[51] Int. Cl.$^2$ ................ A61K 31/445; C07D 455/02; C07D 471/04

[52] U.S. Cl. ................ 424/267; 546/112; 546/138

[58] Field of Search ................ 546/112, 138; 424/267

[56] References Cited

PUBLICATIONS

Winterfeld et al., *Berichte*, 90,863 (1957).

*Primary Examiner*—Alan L. Rotman
*Assistant Examiner*—Richard A. Schwartz
*Attorney, Agent, or Firm*—Gordon W. Hueschen

[57] ABSTRACT

Phenyl- or thienyl-substituted quinolizidines and indolizidines as well as quaternary salts thereof are disclosed. These compounds are useful as pharmaceutical agents exhibiting strong spasmolytic, anti-ulcer, antihistaminic and antiemetic activities with minimized side effects such as thirst and dilation of the pupil.

Phenyl- or thienyl-substituted quinolizidine-methanols and indolizidine-methanols which are starting materials of the aforementioned quinolizidine and indolizidine compounds are also useful as having spasmolytic, anti-ulcer, anti-histaminic and anti-emetic activities.

32 Claims, No Drawings

ANTI-SPASMODIC SUBSTITUTED QUINOLIZIDINE AND INDOLIZIDINE COMPOUNDS

CROSS-REFERENCES TO RELATED APPLICATIONS

The present application is a continuation-in-part of our prior-filed co-pending applications Ser. Nos. 904,498, 904,530, 904,533, 904,534 and 904,535, all filed May 10, 1978, and also of our prior-filed co-pending applications Ser. Nos. 969,400, both filed Dec. 14, 1978, all said prior-filed co-pending applications now abandoned.

BACKGROUND OF THE INVENTION

1. Field of the Invention

The present invention relates to substituted quinolizidine- and indolizidine compounds of the formula (I):

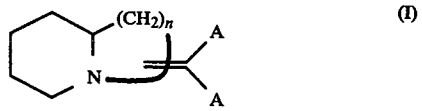

wherein A represents a phenyl group or a 2-thienyl group and n is an integer of 3 or 4, and pharmaceutically acceptable acid addition salts thereof as well as quaternary salts thereof, and to therapeutic compositions containing the same, and further to a method of treating spasm and ulcer therewith.

2. Description of the Prior Art

Atropine has a strong anticholinergic activity and has been used as a spasmolytic agent for a long time. However, clinical use of atropine has been limited because side effects such as thirst, dilation of the pupil, and an increase in blood pressure accompany its use. Therefore, conventional synthetic spasmolytic agents such as diphemanilmethyl sulfate (see, U.S. Pat. No. 2,739,969, and Merck Index, 9th Edition, page 3309), prifinium bromide (see, Merck Index, 9th edition, page 7540), and timepidium bromide (see, J. Med. Chem., vol. 15, page 914(1972) have been proposed and provided for use. These compounds, however, are not satisfactory because their strong anticholinergic main activity is necessarily accompanied by serious undesirable side effects.

SUMMARY OF THE INVENTION

An object of the present invention is to provide a satisfactory therapeutic agent having high anticholinergic activity but minimized side effects, which is the substituted quinolizidine- and indolizidine compound of the formula(I) above.

A further object of the present invention is to provide therapeutic composition containing a compound of the formula(I) which exhibits anticholinergic, antihistaminic, antitussive and analgetic activities, and a method of treating spasm and ulcer, especially spasm-associated ulcer therewith.

DETAILED DESCRIPTION OF THE INVENTION

The quinolizidine- and indolizidine compound of the formula(I) can be prepared by dehydrating the compound represented by the formula(II):

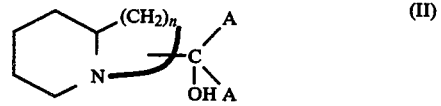

wherein A and n have the same meanings as above, optionally followed by reacting the resulting compounds with pharmaceutically acceptable inorganic or organic acids in a conventional manner or with quaternizing agents of the formula(III):

wherein R is a lower alkyl group; X is a pharmaceutically acceptable anion.

The dehydration of the compound of the formula(II) ordinarily proceeds by heating, preferably at a reflux temperature of the solvent used in an organic solvent in the presence of a dehydrating agent. Any solvent can be employed as long as it does not prevent the dehydration reaction. Typical examples of these solvents are methanol, ethanol, benzene, toluene, etc. Suitable examples of dehydrating agents which are preferably employed in the dehydration include hydrochloric acid, sulfuric acid, phosphorous oxychloride, p-toluenesulfonic acid, etc.

The thus obtained indolizidine- and quinolizidine compound of the formula(I) can be converted into the corresponding acid addition salts, using pharmaceutically acceptable non-toxic acids, e.g., hydrochloric acid, hydrobromic acid, sulfuric acid, oxalic acid, maleic acid, fumaric acid, citric acid, etc.

The compound of the formula(I) exhibits strong spasmolytic, anti-ulcer, anti-histaminic, antitussive and analgetic activities with minimized side effects such as thirst and dilation of the pupil.

The quaternary salt of the compound of the formula(I) can be represented by the formula(IV):

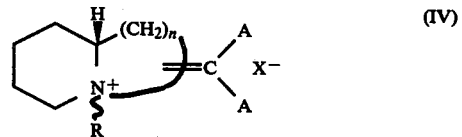

wherein A and n have the same meanings as above and X is the anion of the compound R—X, wherein X is a pharmaceutically acceptable anion, and R is a lower alkyl group.

In the formula(IV), the lower alkyl group R has preferably 1to 3 carbon atoms, inclusive, and specific examples of the loweralkyl group include a methyl group, an ethyl group, a propyl group, etc. Of these, the most preferred are methyl and ethyl groups.

The pharmaceutically acceptable non-toxic anions X are generally acid residues of organic or inorganic acids, such as hydrochloric acid, hydrobromic acid, hydroiodic acid, sulfuric acid, alkyl sulfates, etc. Of these, hydrobromic acid and hydroiodic acid residues are most preferred.

The aforementioned quaternizing reaction can be performed in the presence of or in the absence of solvents. Typical examples of solvents which can be employed in accordance with the present invention are ether, acetone, alcohols such as methanol or ethanol, etc. The quaternizing reaction proceeds at temperatures between about 5° C. and about 100° C., preferably 10° and 40° C., more preferably room temperature (about 20° C.), if necessary in a sealed tube.

The quaternary salt of the formula(IV) includes steric isomers (trans- and cis-isomers), and they can be obtained as a mixture or pure isomer after recrystallization in a conventional manner.

It has been found that the quaternary salt of the formula (IV) possesses strong anticholinergic and anti-ulcer activities but have reduced side effects such as thirst and dilation of the pupil.

It has also been found that the starting material per se of the formula(II) exhibits spasmolytic, anti-histamic, antitussive and analgetic activities. The compound of the formula(II) can also be converted into the corresponding quaternary salt thereof by reacting with the aforementioned quatenizing agent R-X, as in a manner described above, the quarternary salt can be represented by the formula(V):

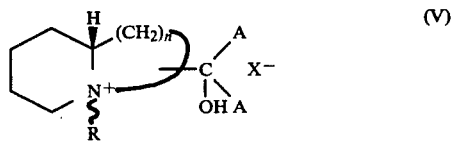

wherein A, R and n each represents the same meanings as defined above. The quarternary salt of the formula(V) is also an excellent antihistaminic, anticholinergic and anti-emetic. When the quaternary salt of the formula(V) is dehydrated as described hereinabove, the quarternary salt of the formula(III) can be obtained, of course.

The compounds of the formula(II) or the starting material for the compounds of the formula(I) are new, except for α,α-diphenylquinolizidine-1-methanol (see, *Chem Ber.*, vol. 90, pages 863–867 (1975)), and can be prepared in conventional manners, such as, by reacting ketones with Grignard reagents with modifications of *Chem Ber.*, identified above, as shown in reaction routes (A) and (B) below, or by reacting esters with Grignard reagents as shown by reaction route (C), below.

The compounds of the present invention represented by the formulae(I), (II), (IV) and (V) exhibit strong spasmolytic, anti-ulcer, anti-histaminic, antitussive and analgetic activities with minimized side effects. The high order of these activities of the active agent of the present invention, together with their reduced side effects, is evidenced by test in lower animals, representative of which are reported herein. The compound of the present invention represented by the formulae(I), (II), (IV) and (V) can be administered per os, e.g., in the form of pills or tablets, in which it may be present together with the usual pharmaceutical carriers, conventionally by compounding the compounds of the present invention together with a customary carrier or adjuvant, such as talc, magnesium stearate, starch, lactose, gelatin, any of numerous gums, and the like. Thus, in their most advantageous form, the compositions of the invention will contain a non-toxic pharmaceutical carrier in addition to the active ingredient of the present invention. Exemplary solid carriers are lactose, magnesium stearate, calcium stearate, starch, terra alba, dicalcium acacia, or the like. Representative liquid carrers are peanut oil, sesame oil, olive oil, water or the like. The active agents of the invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical forms suitable for may modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution.

The method of using the compounds of the present invention comprises internally or externally administering the compounds of the invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 1 to about 100 mg. per unit dose, preferably 3 to 30 mg. for an oral dose, while parenteral dosages are usually less and ordinarily about one-half of

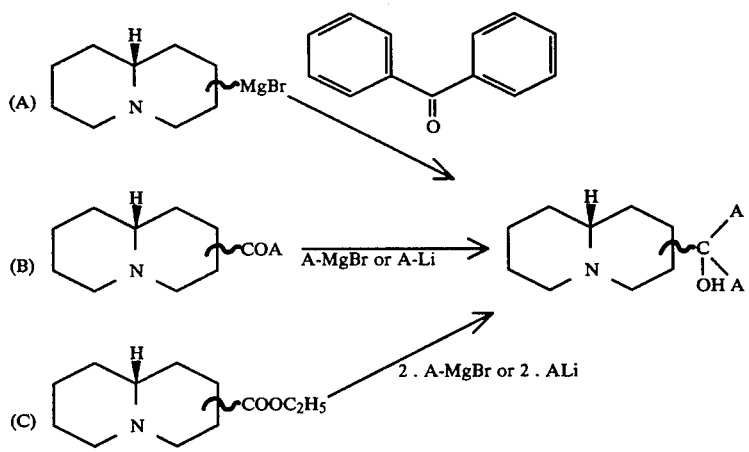

(wherein A have the same meaning as above)

Though representative examples of synthesis are illustrated with reference to quinolizidine compounds, the reactions can also be proceed with indolizidine compounds as well.

the oral dose. The unit dose is preferably given a suitable number of times daily, typically three times. The daily dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make it suitable for wide variations, and the invention therefore should not be limited by the exact ranges stated. The exact dosage, both nit dosage and daily dosage, will of course have to be determined according to established medical principles.

The results of pharmacological tests performed using the compounds of the present invention are shown below.

Test Method:

The $ED_{50}$ values of the compound of the present invention with respect to protective activity against spasm induced by acetylcholine ($1 \times 10^{-7}$ g/ml) were measured using isolated ileum of guinea pigs in accordance with the well-known Magnus method and relative potency was examined by taking the $ED_{50}$ value of atropine as 1.0.

| Compound | Relative Potency |
| --- | --- |
| 2-Diphenylmethylenequinolizidine | 0.09 |
| 2-Diphenylmethylenequinolizidine methyl bromide | 1.12 |
| 3-Diphenylmethylenequinolizidine methyl bromide | 0.58 |
| 3-Diphenylmethylenequinolizidine ethyl bromide | 0.45 |
| 3-(Dithien-2-ylmethylene)quinolizidine methyl bromide | 0.86 |
| 2-(Dithien-2-ylmethylene)indolizidine methyl iodide | 0.32 |
| 2-(Dithien-2-ylmethylene)quinolizidine methyl bromide | 1.16 |
| 1-Diphenylmethyleneindolizidine methyl bromide | 0.09 |
| 1-(Dithien-2-ylmethylene)quinolizidine methyl bromide | 0.26 |
| Atropine | 1.0 |
| Scopolamine n-butyl bromide | 0.02 |
| Diphemanyl methyl sulfate | 0.11 |
| Timepidium bromide | 0.15 |

As can be seen from the results shown in the table above, the compounds of the present invention have stronger protective activity against spasm induced by acetylcholine than commercially available scopolamine, diphenmanyl methyl sulfate and timepidium bromide. The other compounds of this invention also exhibit this high order of antispasmodic activity.

As has been discussed before, atropine which is not actually employed for treatment of spasm-associated ulcer, as well as even commercially available compounds above accompany serious side effects of undesirable nature. Considering as a whole, it will be understood that the compounds of the present invention are excellent therapeutic agents particularly for spasm-associated ulcer.

The present invention will be explained hereinbelow with reference to the examples, which are given by way of illustration only and are not to be construed as limiting.

EXAMPLE 1

2-Diphenylmethylenequinolizidine hydrochloride

To 1.39 g. of α,α-diphenylquinolizidine-2-methanol was added 10 ml. of ethanolic hydrochloride. The resulting mixture was refluxed for 4 hrs. with stirring. The residue remained after the removal of the ethanol by distillation was dissolved in water. The solution was rendered alkaline with a potassium carbonate solution and extracted with chloroform. The chloroform layer was washed with water and dried. After the solvent was removed by distillation, light yellow liquid was obtained. The product was converted into the hydrochloride in a conventional manner. By recrystallization from acetone-ether, 0.47 g. of colorless needle 2-diphenylmethylenequinolizidine hydrochloride showing a melting point of 233° to 235° C. was obtained.

| Elemental Analysis: $C_{22}H_{25}N \cdot HCl$ | | | |
| --- | --- | --- | --- |
| | C | H | N |
| Calcd. | 77.74 | 7.71 | 4.12 |
| Found | 77.48 | 7.59 | 3.78 |

EXAMPLE 2

2-(Diphenylmethylene)quinolizidine methyl iodide

In 10 ml. of acetone was dissolved 0.1 g. of 2-(diphenylmethylene)quinolizidine. After 1.0 ml. of methyl iodide was added to the solution, the mixture was stirred at room temperature of 24 hrs. The precipitated crystals were removed by filtration and recrystallized from methanol to give 0.1 g. of colorless needles having a melting point of 280° to 282° C.(decomposed).

| Elemental Analysis: $C_{22}H_{28}NI$ | | | |
| --- | --- | --- | --- |
| | C | H | N |
| Calcd. | 62.03 | 6.34 | 3.14 |
| Found | 61.97 | 6.43 | 3.13 |

EXAMPLE 3

2-(Diphenylmethylene)quinolizidine methyl bromide (a) In 50 ml. of acetone was dissolved 5.5 g. of 2-(diphenylmethylene)quinolizidine. After adding 5 ml. of methyl bromide thereto, the mixture was allowed to stand for 48 hrs. at room temperature in a sealed tube. After completion of the reaction, the residue obtained by removing the solvent by distillation was recrystallized from a methanol-acetone mixture to obtain 5.34 g. of colorless prisms of the trans isomer, having a melting point of 261° to 263°0 C.(decomposed).

NMR (CDCl$_3$)δ:3.33 (N+—CH$_3$)

| Elemental Analysis: $C_{23}H_{28}NBr$ | | | |
| --- | --- | --- | --- |
| | C | H | N |
| Calcd. | 69.34 | 7.08 | 3.52 |
| Found | 69.08 | 7.16 | 3.26 |

(b) The mother liquor from the recrystallization was distilled to dryness under reduced pressure. The resulting residue was recrystallized from methaol-acetone twice. The combined mother liquors were distilled to dryness under reduced pressure to obtain colorless prisms of the cis isomer; the yield was 1.12 g. and the melting point was 235° to 236° C.

NMR (CDCl$_3$)δ:3.67 (N+—CH$_3$)

EXAMPLE 4

2-(Diphenylmethylene)quinolizidine ethyl bromide: m.p. 233°–234° C. (acetone)

| Elemental Analysis: C$_{24}$H$_{30}$NBr | | | |
|---|---|---|---|
| | C | H | N |
| Calcd. | 69.90 | 7.33 | 3.40 |
| Found | 69.58 | 7.42 | 3.26 |

EXAMPLE 5

3-Diphenylmethylenequinolizidine:

(a) In 20 ml. of 60% sulfuric acid was heated 1.5 g. of α,α-diphenylquinolizidine-3-methanol at 90°–95° C. for 30 mins. with stirring. After completion of the reaction, the reaction product was poured into water. The resulting solution was rendered alkaline with a 10% aq. sodium hydroxide solution and then extracted with ether. The ethereal layer was washed with water and dried. The residue obtained after removing the solvent by distillation was recrystallized from hexane to obtain 1.1 g. of colorless needles showing a melting point of 118° to 120° C.

| Elemental Analysis: C$_{22}$H$_{25}$N | | | |
|---|---|---|---|
| | C | H | N |
| Calcd. | 87.08 | 8.30 | 4.62 |
| Found | 87.30 | 8.33 | 4.48 |

In accordance with the present invention, the product was converted into the hydrochloride in a conventional manner. By recrystallization from methanol, colorless plate-like crystals having melting point of 225° to 228° C. were obtained.

(b) α,α-Diphenylquinolizidine-3-methanol employed as a starting material was prepared in accordance with the following method:

To a solution of phenyl lithium, which had been prepared by the reaction of 1.23 g. of lithium and 16.80 g. of bromobenzene, in 50 ml. of absolute ether was dropwise added a solution of 120 g. of 3-benzoylquinolizidine in absolute ether. The mixture was refluxed for 30 mins. with stirring. After the excess of phenyl lithium was decomposed with water, the reaction mixture was extracted with ether. The thus obtained etheral layer was washed with water and dried. After removing the solvent by distillation, α,α-diphenyl-quinolizidine-3-methanol showing a melting point of 166° to 167° C. was obtained.

EXAMPLE 6

3-Diphenylmethylenequinolizidine methyl iodide:

In 30 ml. of methanol was dissolved 2.0 g. of 3-diphenylmethylenequinolizidine. After adding 1.5 ml. of methyl iodide to the solution, the mixture was stirred at room temperature for 24 hrs. After completion of the reaction, the solvent was distilled off and the resulting crystals were recrystallized from acetone to obtain 1.6 g. of colorless prisms showing a melting point of 221° to 224° C.

| Elemental Analysis: C$_{23}$H$_{28}$NI | | | |
|---|---|---|---|
| | C | H | N |
| Calcd. | 62.03 | 6.34 | 3.14 |
| Found | 61.94 | 6.34 | 3.00 |

EXAMPLE 7

3-Diphenylmethylenequinolizidine methyl bromide:

(a) This compound was prepared in a manner similar to Example 6.

Melting point: 259°–261° C. (decompd., colorless needles)

NMR (CDCl$^3$)δ:2.97(N+—CH$_3$)

| Elemental Analysis: C$_{23}$H$_{28}$NBr | | | |
|---|---|---|---|
| | C | H | N |
| Calcd. | 69.34 | 7.08 | 3.52 |
| Found | 69.60 | 7.29 | 3.26 |

(b) The residue obtained by evaporating to dryness the so obtained mother liquor of the recrystallization above under reduced pressure was recrystallized again from methanol-ether, which procedure was repeated twice to obtain the mother liquor. The combined mother liquors were evaporated to dryness under reduced pressure. The resulting residue was recrystallized from methanol-ether to give colorless crystals having a melting point of 256° to 259° C.

NMR (CDCl$_3$)δ:3.40(N+—CH$_3$)

| Elemental Analysis: C$_{23}$H$_{28}$NBr | | | |
|---|---|---|---|
| | C | H | N |
| Calcd. | 69.34 | 7.08 | 3.52 |
| Found | 69.06 | 6.20 | 3.48 |

EXAMPLE 8

3-Diphenylmethylenequinolizidine ethyl bromide:

This compound was prepared in a manner similar to Example 6.

Melting point: 225°–228° C. (from acetone)

| Elemental Analysis: C$_{24}$H$_{30}$NBr | | | |
|---|---|---|---|
| | C | H | N |
| Calcd. | 69.90 | 7.33 | 3.40 |
| Analysis | 69.87 | 7.36 | 3.27 |

EXAMPLE 9

1-Diphenylmethylenequinolizidine sulfate:

3.5 g. of α,α-diphenylmethylenequinolizidine-1-methanol was heated together with 35 ml. of 60% sulfuric acid at about 100° C. for 20 mins. The reaction mixture was poured into water. After the mixture was rendered alkaline with a 20% aq. sodium hydroxide, the mixture was extracted with ether. The ethereal layer was washed with water and dried. The residue(3.1 g.) obtained after removing the solvent by distillation was treated with ethanolic sulfuric acid. By recrystallization of the thus obtained sulfate from ethanol, colorless needle crystals having a melting point of 219° to 221° C. were obtained.

| Elemental Analysis: $C_{22}H_{25}N \cdot H_2SO_4$ | | | |
|---|---|---|---|
| | C | H | N |
| Calcd. | 65.81 | 6.78 | 3.49 |
| Found | 65.78 | 6.92 | 3.24 |

EXAMPLE 10

1-Diphenylmethylenequinolizidine methyl iodide:

In 20 ml. of acetone was dissolved 0.5 g. of 1-diphenyl-methylenequinolizidine. After 1.0 ml. of methyl iodide was added to the solution, the mixture was allowed to stand for 10 mins. The crystals precipitated were taken out by filtration. By recrystallization of the thus obtained crystals (0.53 g.) from methanol, colorless plate-like crystals having a melting point of 294° to 296° C. (decompd.) were obtained.

| Elemental Analysis: $C_{23}H_{28}NI$ | | | |
|---|---|---|---|
| | C | H | N |
| Calcd. | 62.03 | 6.34 | 3.14 |
| Found | 61.92 | 6.41 | 2.82 |

EXAMPLE 11

1-Diphenylmethylenequinolizidine methyl bromide:

This compound was prepared in accordance with the procedures similar to Example 10.
Melting point: >300° C. (from ethanol)
NMR (CDCl$_3$) δ: 3.19 (N$^+$—CH$_3$)

| Elemental Analysis: $C_{23}H_{28}NBr$ | | | |
|---|---|---|---|
| | C | H | N |
| Calcd. | 69.34 | 7.08 | 3.52 |
| Found | 69.29 | 7.19 | 3.27 |

EXAMPLE 12

1-Diphenylmethylenequinolizidine ethyl bromide:

This compound was prepared in a manner similar to Example 10.
Melting point: >300° C. (from ethanol)

| Elemental Analysis: $C_{24}H_{30}NBr \cdot \frac{1}{2}H_2O$ | | | |
|---|---|---|---|
| | C | H | N |
| Calcd. | 68.40 | 7.41 | 3.32 |
| Found | 68.61 | 7.31 | 3.24 |

EXAMPLE 13

2-Diphenylmethyleneindolizidine:

This compound was prepared in a manner similar to Example 9.
Melting point: 76°–79° C. (from n-hexane, colorless needles)

| Elemental Analysis: $C_{21}H_{23}N$ | | | |
|---|---|---|---|
| | C | H | N |
| Calcd. | 87.15 | 8.01 | 4.84 |
| Found | 87.08 | 8.14 | 4.76 |

EXAMPLE 14

In a manner similar to Example 10, the following compounds were prepared:

(i) 2-Diphenylmethyleneindolizidine methyl iodide:

Melting point: 242°–244° C. (from methanol-acetone, colorless needles)

| Elemental Analysis: $C_{22}H_{26}NI$ | | | |
|---|---|---|---|
| | C | H | N |
| Calcd. | 61.26 | 6.08 | 3.25 |
| Found | 61.00 | 6.15 | 3.13 |

(ii) 2-Diphenylmethyleneindolizidine methyl bromide:

Melting point: 267°–269° C. (from methanol-acetone, decomposed)
NMR (CDCl$_3$) δ: 3.08 (N$^+$–CH$_3$)

| Elemental Analysis: $C_{22}H_{26}NBr$ | | | |
|---|---|---|---|
| | C | H | N |
| Calcd. | 68.75 | 6.82 | 3.64 |
| Found | 68.57 | 6.82 | 3.53 |

EXAMPLE 15

2-(Dithien-2-ylmethylene)indolizidine

To 2.66 g. of α,α-(dithien-2-yl)indolizidine-2-methanol was added to 20 ml. of ethanolic hydrochloric acid. The mixture was stirred for 1.5 hr. with heating at 60° C. Water was added to the residue obtained after removing ethanol by distillation to dissolve. Thereafter, the solution was rendered alkaline with a 10% aq. sodium hydroxide solution and then extracted with ether. The etherial layer was washed with water and dried. The residue remained after removing the solvent by distillation was distilled to obtain 1.76 g. of yellow liquid showing a boiling point of 195° to 197° C. (3 mmHg). The product was converted into the hydrochloride in a conventional manner. By recrystallization from isopropanol, yellow prisms having a melting point of 197° to 200° C. (decompd.) were obtained.

| Elemental Analysis: $C_{17}H_{19}NS_2 \cdot HCl$ | | | |
|---|---|---|---|
| | C | H | N |
| Calcd. | 60.42 | 5.97 | 4.14 |
| Found | 60.17 | 6.12 | 3.87 |

EXAMPLE 16

2-(Dithien-2-ylmethylene)quinolizidine

To 0.7 g. of α,α-(dithien-2-yl)quinolizidine-3-methanol was added 6 ml. of ethanolic hydrochloride. The mixture was heated at 60° C. for 30 mins. with stirring. Then, the residue obtained in a manner similar to Example 1 was recrystallized from isopropyl ether to obtain 0.4 g. of colorless needles showing a melting point of 128°–130° C.

Elemental Analysis: $C_{18}H_{21}NS_2$

|  | C | H | N |
|---|---|---|---|
| Calcd. | 68.53 | 6.71 | 4.44 |
| Found | 68.35 | 6.74 | 4.36 |

EXAMPLE 17

2-(Dithien-2-ylmethylene)indolizidine methyl iodide

In 5 ml. of acetone was dissolved 0.37 g. of 2-(dithien-2-ylmethylene)indolizidine. To the resulting solution was added 1.0 ml. of methyl iodide. The mixture was stirred at room temperature for 3 hrs. The formed crystals were taken out by filtration. By recrystallization from isopropanol, 0.15 g. of colorless or light brown prisms having a melting point of 222° to 225° C. were obtained.

Elemental Analysis: $C_{18}H_{22}INS_2$

|  | C | H | N |
|---|---|---|---|
| Calcd. | 48.76 | 5.00 | 3.16 |
| Found | 48.60 | 5.04 | 2.85 |

EXAMPLE 18

In a manner similar to Example 16, the following compounds were prepared.

(i) 2-(Dithien-2-ylmethylene)indolizidine methyl bromide

Melting point: 200°–202° C. (from isopropanol)
NMR (CDCl$_3$) δ: 3.49 (N$^+$—CH$_3$)

Elemental Analysis: $C_{18}H_{22}BrNS_2 \cdot 1/5 H_2O$

|  | C | H | N |
|---|---|---|---|
| Calcd. | 54.05 | 5.64 | 3.50 |
| Found | 54.02 | 5.59 | 3.24 |

(ii) 2-(Dithien-2-ylmethylene)indolizidine ethyl bromide

Melting point: 212°–214° C. (from isopropanol-acetone)
Elemental Analysis: $C_{19}H_{24}BrNS_2$ Elemental Analysis: $C_{19}H_{24}BrNS_2$

|  | C | H | N |
|---|---|---|---|
| Calcd. | 55.60 | 5.89 | 3.41 |
| Found | 55.33 | 5.91 | 3.16 |

EXAMPLE 19

In a manner similar to Example 17, the following compounds were prepared.

(i) 3-(Dithien-2-ylmethylene)quinolizidine methyl iodide

Melting point: 223°–224° C. (from ethanol)

Elemental Analysis: $C_{19}H_{24}INS_2$

|  | C | H | N |
|---|---|---|---|
| Calcd. | 49.89 | 5.29 | 3.06 |
| Found | 49.66 | 5.35 | 2.72 |

(ii) 3-(Dithien-2-ylmethylene)quinolizidine methyl bromide

Melting point: 278°–280° C. (from ethanol: decompd.)
NMR (CDCl$_3$) δ: 2.92 (N$^+$—CH$_3$)

Elemental Analysis: $C_{19}H_{24}Br NS_2$

|  | C | H | N |
|---|---|---|---|
| Calcd. | 55.60 | 5.89 | 3.41 |
| Found | 55.78 | 5.89 | 3.37 |

(iii) 3-(Dithien-2-ylmethylene)quinolizidine ehtyl bromide

Melting point: 226°–228° C. (from isopropanol-acetone: decompd.)

Elemental Analysis:

|  | C | H | N |
|---|---|---|---|
| Calcd. | 56.12 | 6.22 | 3.27 |
| Found | 56.13 | 6.18 | 3.04 |

EXAMPLE 20

1-(Dithien-2-ylmethylene)quinolizidine hydrochloride

To 1.40 g. of α, α-(dithien-2-yl)quinolizidine-1-methanol was added 15 ml. of ethanolic hydrochloric acid. The mixture was stirred for 1 hr. at 60° C. The residue obtaned by removing the solvent by distillation was dissolved in water. The solution was rendered alkaline with a 10% aq. sodium hydroxide and then extracted with ether. The ethereal layer was washed with water and dried. After removing the solvent by distillation, 1.29 g. of light brown liquid was obtained. The product was converted into the hydrochloride in a conventional manner. By recrystallization from isopropanol-isopropyl ether, the desired light brown prism hydrochloride showing a melting point of 194°–197° C. was obtained.

Elemental Analysis: $C_{18}H_{21}NS_2 \cdot HCl$

|  | C | H | N |
|---|---|---|---|
| Calcd. | 61.43 | 6.30 | 3.98 |
| Found | 61.13 | 6.64 | 3.84 |

EXAMPLE 21

2-(Dithien-2-ylmethylene)quinolizidine

This compound was prepared from α,α-(dithien-2-yl)-quinolizidine-2-methanol in a manner similar to Example 20 except that potassium hydroxide was used in place of sodium hydroxide and chloroform was used for the extraction in place of ether.

Colorless crystals having a melting point of 88°–90° C. (from isopropyl ether)

| Elemental Analysis: $C_{18}H_{21}NS_2$ | | | |
|---|---|---|---|
| | C | H | N |
| Calcd. | 68.53 | 6.71 | 4.44 |
| Found | 68.34 | 6.72 | 4.26 |

EXAMPLE 22

1-Diphenylmethyleneindolizidine

A mixture of 3.2 g. of α,α-diphenylindolizidine-1-methanol and 20 ml. of 60% sulfuric acid was heated at 80° C. for 1.5 hr. with stirring. After completion of the reaction, the reaction mixture was poured into water. The reaction mixture was rendered alkaline with a 20% aqueous sodium hydroxide solution and then extracted with ether. The ethereal layer was washed with water and dried. After the removal of the solvent by distillation, 2.9 g. of light yellow viscous substance was obtained.

Mass spectroanalysis: $C_{21}H_{23}N$ m/e: 289 (M+), 212.

α,α-Diphenylindolizidine-1-methanol employed as a starting material was prepared as follows:

To a phenyl lithium solution prepared by dissolving 0.51 g. of metallic lithium and 6.32 g. of bromobenzene in 50 ml. of absolute ether, was dropwise added a solution of 2.40 g. of 1-ethoxycarbonylindolizidine in 20 ml. of absolute ether under ice cooling. After refluxing for about 10 mins., water was dropwise added thereto, followed by extraction with ether. The ethereal layer was further extracted with dil. hydrochloric acid. The aqueous layer was rendered alkaline with an aq. sodium hydroxide solution and then extracted with ether. The ethereal layer was washed with water and dried. After removing the solvent by distillation, 3.58 g. of light yellow viscous substance was obtained.

Mass spectrum: $C_{21}H_{25}NO$ m/e/ : 307 (M+), 230, 123 (basic peak).

The product was a mixture of two diastereoisomers and used for the reaction above as it was.

EXAMPLE 23

1-(Dithien-2-ylmethylene)quinolizidine methyl iodide

To a solution of 0.3 g. of 1-(dithien-2-ylmethylene)-quinolizidine in 5 ml. of anhydrous acetone was added 1 ml. of methyl iodide. The mixture was stirred at room temperature for 1 hr. The formed crystals were collected by filtration. By recrystallizing from isopropanol, 0.3 g. of light brown needles having a melting point of 284°-285° C. (decompd.) were obtained.

| Elemental Analysis: $C_{19}H_{24}INS_2$ | | | |
|---|---|---|---|
| | C | H | N |
| Calcd. | 49.89 | 5.29 | 3.06 |
| Found | 50.02 | 5.48 | 2.99 |

EXAMPLE 24

In a manner similar to Example 23, the following compounds were prepared.

(i) 1-(Dithien-2-ylmethylene)quinolizidine methyl bromide

Melting point: 294°-297° C. (from ethanol-isopropyl ether, decomposed)
NMR (CDCl₃) δ: 3.36 (N+—CH₃)

| Elemental Analysis: $C_{19}H_{24}BrNS_2$ | | | |
|---|---|---|---|
| | C | H | N |
| Calcd. | 55.60 | 5.89 | 3.41 |
| Found | 55.18 | 6.11 | 3.54 |

(ii) 1-(Dithien-2-ylmethylene)quinolizidine ethyl bromide

Melting point: 286°-288° C. (from ethanol-isopropyl ether, decomposed)

| Elemental Analysis: $C_{20}H_{26}BrNS_2$ | | | |
|---|---|---|---|
| | C | H | N |
| Calcd. | 56.59 | 6.17 | 3.30 |
| Found | 56.79 | 6.54 | 3.13 |

EXAMPLE 25

2-(Dithien-2-ylmethylene)quinolizidine methyl bromide

In 5 ml. of acetone was dissolved 0.5 g. of 2-(dithien-2-ylmethylene)quinolizidine. To the resulting solution was added 2.0 ml. of methyl bromide. The mixture was stirred at room temperature for 24 hrs. The formed crystals were taken out by filtration. By recrystallizing from ethanol, 0.49 g. of colorless crystals showing a melting point of 246°-248° C. (decomposed) were obtained.

NMR (CDCl₃) δ: 3.42 (N+—CH₃)

| Elemental Analysis: $C_{19}H_{24}BrNS_2$ | | | |
|---|---|---|---|
| | C | H | N |
| Calcd. | 55.60 | 5.89 | 3.41 |
| Found | 55.31 | 5.88 | 3.10 |

EXAMPLE 26

2-(Dithien-2-ylmethylene)quinolizidine

This compound was prepared in a manner similar to Example 25 above except that the reaction mixture was heated at 50° C. in a sealed tube.

Colorless crystals having a melting point of 217°-218° C. (from isopropanol)

| Elemental Analysis: $C_{20}H_{26}BrNS_2$ | | | |
|---|---|---|---|
| | C | H | N |
| Calcd. | 56.59 | 6.17 | 3.30 |
| Found | 56.30 | 6.15 | 3.31 |

EXAMPLE 27

1-Diphenylmethyleneindolizidine methyl bromide

In 10 ml. of acetone was dissolved 0.5 g. of 1-diphenylmethyleneindolizidine. To the resulting solution was added 2 ml. of methyl bromide. The mixture was allowed to stand for 30 mins. The crystals obtained after distilling of the solvent were washed with acetone to obtain 540 mg. of colorless plate-like crystals showing a melting point of 210°-211° C. were obtained.

NMR (CDCl₃) δ: 3.49 (N+—CH₃)

| Elemental Analysis: $C_{22}H_{26}NBr$ | | | |
|---|---|---|---|
| | C | H | N |
| Calcd. | 68.75 | 6.82 | 3.64 |
| Found | 68.56 | 6.85 | 3.51 |

EXAMPLE 28

In a manner similar to Example 27, the following compounds were obtained.

(i) 1-(Diphenylmethyleneindolizidine methyl iodide

Melting point: 189°–190° C. (colorless needles)

(ii) 1-Diphenylmethyleneindolizidine ethyl bromide

Melting point: 163°–164° C. (colorless plate-like crystals)

EXAMPLE 29

2-[1,1-Diphenyl-1-hydroxymethyl] (e)-trans-quinolizidine

A solution of 5.3 g. of 2-benzoyl (e)-trans-quinolizidine in dry ether was dropwise added to a solution of phenyl lithium prepared from 0.46 g. of lithium and 5.2 g. of bromobenzene in dry ether. The mixture was heated under reflux for 15 mins. After completion of the reaction, the reaction mixture was mixed with water and then ether was evaporated off by distillation. The residue was added to n-hexane to precipitate out crystals which were then collected by filtration and washed with water and then with n-hexane. After drying, 4.76 gl of colorless crystals were obtained. Recrystallization from isopropanol gave colorless plate-like crystals with a melting point of 188°–189° C.

IR (KBr) : 3400 cm$^{-1}$ (OH)

| Elemental Analysis: $C_{22}H_{27}NO \cdot \frac{1}{2}H_2O$ | | | |
|---|---|---|---|
| | C | H | N |
| Calcd. | 81.06 | 8.50 | 4.30 |
| Found | 81.11 | 8.63 | 4.30 |

EXAMPLE 30

2-[1,1-Diphenyl-1-hydroxymethyl] (e)-trans-quinolizidine

A solution of 5.3 g. of 2-ethoxycarbonyl (e)-trans-quinolizidine in dry ether was dropwise added to a solution of phenyl lithium prepared from 0.39 g. of lithium and 4.79 g. of bromobenzene in dry ether. The mixture was refluxed for 30 mins. and then treated in the manner of Example 29 to give 2.77 g. of colorless crystals. Recrystallization from isopropanol gave colorless plate-like crystals with a melting point of 188°–189° C. This compound was consistent with the product of Example 29 in IR and TLC and did not show depression of the melting point.

EXAMPLE 31

3-[1,1-Diphenyl-1-hydroxymethyl] (a)-trans-quinolizidine and
3-[1,1-diphenyl-1-hydroxymethyl] (e)-trans-quinolizidine 3-Ethoxycarbonyl-trans-quinolizidine (34.8 g.) were treated in the manner of Example 30 to give 45.6 g. of colorless crystals. Recrystallization from isopropanol gave (A) 3-[1,1-diphenyl-1-hydroxymethyl] (a)-trans-quinolizidine as colorless needle-like crystals with a melting point of 188°–189.5° C. and (B) 3-[1,1-diphenyl-1-hydroxymethyl] (e)-trans-quinolizidine as colorless plate-like crystals with a melting point of 166°–167° C.

(A) IR (CHCl$_3$): about 3000 cm$^{-1}$ (OH)

| Elemental Analysis: $C_{22}H_{27}NO$ | | | |
|---|---|---|---|
| | C | H | N |
| Calcd. | 82.20 | 8.47 | 4.36 |
| Found | 82.07 | 8.53 | 4.49 |

(B) IR (CHCl$_3$) : 3600 cm$^{-1}$ (OH)

| Elemental Analysis: $C_{22}H_{27}NO$ | | | |
|---|---|---|---|
| | C | H | N |
| Calcd. | 82.20 | 8.47 | 4.36 |
| Found | 82.24 | 8.62 | 4.40 |

EXAMPLE 32

3-[1,1-Diphenyl-1-hydroxymethy] (e)-trans-quinolizidine

3-Benzoyl (e)-trans-quinolizidine was treated in the manner of Example 29. The so-obtained colorless crystals were re-crystallized from isopropanol to give colorless plate-like crystals with a melting point of 166°–167° C. This compound was consistent with the compound (B) obtained in Example 31 in IR and TLC and did not show depression of the melting point.

EXAMPLE 33

3-[1,1-Diphenyl-1-hydroxymethyl] (a)-trans-quinolizidine methyl bromide

A mixture of 0.4 g. of 3-[1,1-diphenyl-1-hydroxymethyl]-(a)-trans-quinolizidine and 0.4 ml. of methyl bromide was heated at 40°–45° C. for two days in a sealed tube. Then, an excess of methyl bromide was removed by distillation under reduced pressure, whereby crystals were precipitated out. The crystals were recrystallized from methanol-ether to give 0.39 g. of colorless needle crystals having a melting point above 300° C.

In a similar manner, 0.17 g. of 3-(1,1-diphenyl-1-hydroxymethyl) (e)-trans-quinolizidine methyl bromide with a metling point of above 300° C. (from methanol-ether) was prepared, except that a mixture of 0.2 g. of the corresponding (e)-trans-quinolizidine, 3 ml. of methyl bromide and 10 ml. of methanol was allowed to stand for two days at room temperature, followed by removal of the excess methanol and methyl bromide.

EXAMPLE 34

In the manner of Example 33, the following compound was prepared.

2-(1,1-Diphenyl-1-hydroxymethyl) (e)-trans-quinolizidine methyl iodide m.p. 275°–278° C. (methanol-acetone)

EXAMPLE 35

3-[1,1-(Dithien-2-yl)-1-hydroxymethyl] (a)-trans-quinolizidine

A solution of 0.34 g. of 3-(thenoyl) (a)-trans-quinolizidine in dry ether was dropwise added to a solution of thienyl magnesium bromide prepared from 0.5 g. of magnesium and 0.35 g. of 2-bromothiophene in dry ether under cooling and then heated under reflux for 3 hrs. After completion of the reaction, water was added to the reaction mixture. The ethereal layer was separated and extracted with 10% aqueous hydrochloric acid. The aqueous layer was adjusted to alkaline by adding a sodium hydroxide solution and then extracted with chloroform. The chloroform layer was washed with water and dried. After evaporation of the solvent, the residue was recrystallized from isopropyl ether to obtain 0.55 g. of colorless needles of m.p. 147°–148° C.

| Elemental Analysis: $C_{18}H_{23}NOS_2$ | | | |
| --- | --- | --- | --- |
| | C | H | N |
| Calcd. | 64.82 | 6.95 | 4.20 |
| Found | 64.91 | 7.04 | 3.96 |

EXAMPLE 36

2-[1,1-(Dithien-2-yl)-1-hydroxymethyl](e)-trans-quinolizidine:

A solution of 3.80 g. of 2-ethoxycarbonyl (e)-trans-quinolizidine in dry tetrahydrofuran was added to a solution of thienyl magnesium bromide prepared from 1.35 g. of magnesium and 8.80 g. of 2-bromothiophene in dry tetrahydrofuran. The resulting mixture was stirred. After completion of the reaction, the mixture was mixed with a sodium hydroxide solution and filtered. The filtrate was concentrated and mixed with water and ether. The ethereal layer was separated and extracted with a 5% aqueous hydrochloric acid solution. After adjusting the aqueous layer to be alkaline with an aqueous sodium hydroxide solution, the aqueous layer was extracted with ether. The ethereal layer was washed with water and dried. The solvent was distilled off and the residue was recrystallized from a benzene-isopropyl ether solvent mixture to obtain 4.64 g. of colorless prism-like crystals having a melting point of 149°–150° C.

| Elemental Analysis: $C_{18}H_{23}NOS_2$ | | | |
| --- | --- | --- | --- |
| | C | H | N |
| Calcd. | 64.82 | 6.95 | 4.20 |
| Found | 64.99 | 6.96 | 3.85 |

EXAMPLE 37 rel-(2S, 8aR)-2-[1,1-(Dithien-2-yl)-1-hydroxymethyl]-indolizidine:

A solution of 0.37 g. of rel-(2S, 8aR)-2-ethoxycarbonyl-indolizidine in dry ether was dropwise added to a solution of thienyl magnesium bromide prepared from 0.14 g. of magnesium and 1.8 g. of 2-bromothiophene in dry ether under cooling and stirred at room temperature for 10 mins. After completion of the reaction, the reaction mixture was mixed with water and extracted with ether. The ethereal layer was washed with water and dried. After removing the solvent by distillation, the residue was recrystallized from isopropyl ether to give 0.10 g. of colorless needles with a melting point of 130°–131° C.

IR (CHCl$_3$) : about 3200 cm$^{-1}$ (OH)

| Elemental Analysis: $C_{17}H_{21}NOS_2$ | | | |
| --- | --- | --- | --- |
| | C | H | N |
| Calcd. | 63.91 | 6.63 | 4.38 |
| Found | 63.61 | 6.65 | 4.13 |

EXAMPLE 38 rel-(2S, 8aR)-2-(1,1-Diphenyl-1-hydroxymethyl)indolizidine(A) and rel-(2S, 8aR)-2-(1,1-diphenyl-1-hydroxymethyl)indolizidine(B)

2-Benzoylindolizidine was added to a solution of phenyl lithium prepared from 1.09 g. of metal lithium and 12.3 g. of bromobenzene in dry ether. The mixture was heated under reflux for 20 mins. After completion of the reaction, the reaction mixture was mixed with water and dried. The solvent was distilled off and the residue was mixed with nOhexane. The resulting crystals were filtered under suction to give 11.75 g. of colorless crystals. By recrystallization from isopropyl ether, colorless needles (A) with a melting point of 136°–138° C. were obtained.

IR (CHCl$_3$) : 3600 cm$^{-1}$ (OH)

| Elemental Analysis: $C_{21}H_{25}NO$ | | | |
| --- | --- | --- | --- |
| | C | H | N |
| Calcd. | 82.04 | 8.20 | 4.56 |
| Found | 81.91 | 8.23 | 4.44 |

The mother liquor from the recrystallization was evaporated off under reduced pressure to dryness and the residue was recrystallized from isopropyl ether to give colorless needles (B) with a melting point of 132°–134° C.

IR (CHCl$_3$) : about 3200 cm$^{-1}$

| Elemental Analysis: $C_{21}H_{25}NO$ | | | |
| --- | --- | --- | --- |
| | C | H | N |
| Calcd. | 82.04 | 8.20 | 4.56 |
| Found | 81.87 | 8.06 | 4.33 |

EXAMPLES 39–43

1-(1,1-Diphenyl-1-hydroxymethyl)indolizidine

A solution of 2.40 g. of 1-ethoxycarbonylindolizidine in 20 ml. of dry ether was dropwise added to a solution of phenyl lithium prepared from 0.51 g. of metal lithium, 6.32 g. of bromobenzene and 50 ml. of dryether under ice cooling. After refluxing for about 10 mins., water was dropwise added to the reaction mixture. The mixture was extracted with ether. The ethereal layer was extracted with a diluted hydrochloric acid solution and the aqueous layer was adjusted to alkaline with a causting soda solution and then extracted with ether. The ethereal layer was washed with water and dried. After removing the solvent by distillation, 3.58 g. of yellowish viscous substance was obtained. This substance was crystallized. By recrystallization from isopropyl ether, colorless needles with a melting point of 120°–121° C. was obtained.

| Elemental Analysis: $C_{21}H_{25}NO$ | | | |
|---|---|---|---|
|  | C | H | N |
| Calcd. | 82.04 | 8.20 | 4.56 |
| Found | 81.92 | 8.29 | 4.40 |

Mass spectrograph: $C_{21}H_{25}NO$
m/e : 307 (M+), 230 123 (base peak)
This product was a mixture of two diastereoisomers.
Compounds (40)–(43) below were prepared according to the same method as described in the above example.

| Compound | | Physical Data |
|---|---|---|
| (40) | 1-[1,1-(Dithien-2-yl)-1-hydroxymethyl](a)-trans-quinolizidine | m.p. 186°–187° C. (isopropyl ether) |
| (41) | 3-[1,1-(Dithien-2-yl)-1-hydroxymethyl](e)-trans-quinolizidine | m.p. 176°–77° C. (isopropanol-isopropyl ether) |
| (42) | rel-(2R, 8aR)-2-[1,1-(Dithien-2-yl)-1-hydroxymethyl]indolizidine | m.p. 101°–102° C. IR (CHCl₃): 3590 cm⁻¹(OH) (isopropyl ether) |
| (43) | 1-[1,1-(Dithien-2-yl)-1-hydroxy-methylindolizidine | m.p. 139°–140° C. (mixture of two diastereo-isomers) (isopropyl ether) |

EXAMPLES 44–49

1-[1,1-(Dithien-2-yl)-1-hydroxymethyl] (a)-trans-quinolizidine methyl bromide:

A solution of 0.05 g. of 1-[1,1-(dithien-2-yl)-1-hydroxymethyl] (a)-trans-quinolizidine in 2 ml. of acetone was added to 1.0 ml. of methyl bromide and stirred at room temperature for 60 hrs. The crystals separated out was filtered and recrystallized from acetone-methanol to give 0.03 g. of colorless prism crystals with a melting point of 167°–170° C. (decomposed).

| Elemental Analysis: $C_{19}H_{26}Br\ NOS_2$ | | | |
|---|---|---|---|
|  | C | H | N |
| Calcd. | 53.26 | 6.12 | 3.27 |
| Found | 52.96 | 6.15 | 3.21 |

Compounds (45)–(49) below were prepared according to the same method as described in the above example.

| Compound | | Physical Data |
|---|---|---|
| (45) | 2-[1,1-(Dithien-2-yl)-1-hydroxymethyl](e)-trans-quinolizidine methyl bromide | m.p. 253°–255° C. (acetone-methanol) |
| (46) | 3-[1,1-(Dithien-2-yl)-1-hydroxymethyl](a)-trans-quinolizidine methyl bromide | m.p. 272°–273° C. (decompd.) (decompd.) (ethanol) |
| (47) | 3-[m.p. 286°–288° C. methyl](3)-trans-quinolizidine methyl bromide | (decomposed) (acetone-methanol) |
| (48) | 1-(1,1-Diphenyl-1-hydroxymethyl)-(a)-trans-quinolizidine methyl bromide | m.p. >300° C. (methanol-ether) |
| (49) | 2-(1,1-Diphenyl-1-hydroxymethyl)-indolizidine methyl chloride | m.p. >300° C. (methanol-acetone) |

While the invention has been described in detail and with reference to specific embodiments thereof, it will be apparent to one skilled in the art that various changes and modifications can be made therein without departing from the spirit and scope thereof.

What is claimed is:

1. A compound selected from quinolizidine- and indolizidine compounds of the formula:

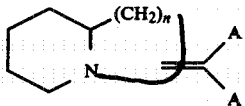

wherein A represents a phenyl group or a 2-thienyl group, n is an integer of 3 or 4, and a pharmaceutically acceptable acid addition salt thereof, and quaternary ammonium salt thereof.

2. A compound as claimed in claim 1 wherein n represents 4.

3. A pharmaceutical composition useful as an antispasmodic comprising an effective antispasmodic amount of a compound of claim 2, together with a pharmaceutically acceptable carrier.

4. Method of treating spasm or spasm-associated ulcer in a patient afflicted therewith, which comprises the step of administering to said patient an effective antispasmodic amount of a compound of claim 2.

5. 2-Diphenylmethylenequinolizidine.

6. Methyl bromide of the compound of claim 5.

7. 3-Diphenylmethylenequinolizidine.

8. Methyl bromide of the compound of claim 7.

9. 2-(Dithien-2-ylmethylene)quinolizidine.

10. Methyl bromide of the compound of claim 9.

11. 3-(Dithien-2-ylmethylene)quinolizidine.

12. Methyl bromide of the compound of claim 11.

13. A compound as claimed in claim 1 wherein n represents 3.

14. A pharmaceutical composition useful as an antispasmodic comprising an effective antispasmodic amount of a compound of claim 13, together with a pharmaceutically acceptable carrier.

15. Method of treating spasm or spasm-associated ulcer in a patient afflicted therewith, which comprises the step of administering to said patient an effective antispasmodic amount of a compound of claim 13.

16. 2-Diphenylmethyleneindolizidine.

17. Methyl bromide of the compound of claim 16.

18. 2-(Dithien-2-ylmethylene)indolizidine.

19. Methyl bromide of the compound of claim 18.

20. A compound selected from indolizidine-methanol compounds of the formula:

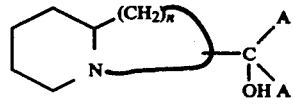

wherein A represents a phenyl group or a 2-thienyl group, n is 3, and a pharmaceutically acceptable acid addition salt thereof, and a quaternary ammonium salt thereof.

21. A pharmaceutical composition useful as an antispasmodic comprising an effective antispasmodic amount of a compound of claim 20, together with a pharmaceutically acceptable carrier.

22. Method of treating spasm or spasm-associated ulcer in a patient afflicted therewith, which comprises the step of administering to said patient an effective antispasmodic amount of a compound of claim 20.

23. A compound of claim 20, which is 2-(1,1-Diphenyl-1-hydroxymethyl)-indolizidine methyl bromide.

24. A compound selected from quinolizidine-methanol compounds of the formula

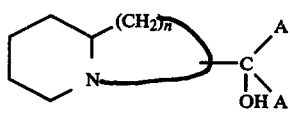

wherein n is 4, wherein A represents a 2-thienyl group, wherein A may also represent a phenyl group when the diphenylhydroxy methyl radical is present in the 2- or 3-position of said quinolizidine, ring and a pharmaceutically acceptable acid addition salt thereof, and a quaternary ammonium salt thereof.

25. A pharmaceutical composition useful as an antispasmodic comprising an effective antispasmodic amount of a compound of claim 24, together with a pharmaceutically acceptable carrier.

26. Method of treating spasm or spasm-associated ulcer in a patient afflicted therewith, which comprises the step of administering to said patient an effective antispasmodic amount of a compound of claim 24.

27. A compound of claim 24, which is 1-[1,1-(Dithien-2-yl)-1-hydroxymethyl]-trans-quinolizidine methyl bromide.

28. A compound of claim 24, which is 2-[1,1-(Dithien-2-yl)-1-hydroxymethyl]-trans-quinolizidine methyl bromide.

29. A compound of claim 24, which is 3-[1,1-(Dithien-2-yl)-1-hydroxymethyl]-trans-quinolizidine methyl bromide.

30. A compound of claim 24, which is 2-(1,1-Diphenyl-1-hydroxymethyl)-trans-quinolizidine methyl iodide.

31. A compound of claim 24, which is 3-(1,1-Diphenyl-1-hydroxymethyl) (a)-trans-quinolizidine methyl bromide.

32. A compound of claim 24, which is 3-(1,1-Diphenyl-1-hydroxymethyl) (e)-trans-quinolizidine methyl bromide.

* * * * *

UNITED STATES PATENT AND TRADEMARK OFFICE
CERTIFICATE OF CORRECTION

PATENT NO. : 4,205,074
DATED : May 27, 1980
INVENTOR(S) : Hideo Kato and Eiichi Koshinaka It is certified that error appears in the above-identified patent and that said Letters Patent is hereby corrected as shown below:

Col. 1, line 13; "969,400," should read -- 969,400 and 969,401 --.

Col. 2, line 11; "manner or" should read -- manner, or --
Col. 3, line 11; "thirst" should read -- thirsty --
Col. 3, line 17; "quatenizing" should read -- quaternizing --
Col. 3, line 18; "quarternary" should read -- quaternary --
Col. 3, line 28; "n" should read -- $\underline{n}$ --
Col. 3, line 29; "quarternary" should read -- quaternary --
Col. 3, line 33; "quarternary" should read -- quaternary --
Col. 3, line 38; "(1975))" should read -- (1957)) --
Col. 4, line 23; "water or" should read -- water, or --
Col. 5, line 53; "diphenmanyl" should read -- diphemanyl --
Col. 6, line 55; "263°0 C." should read -- 263°C. --
Col. 6, line 66; "methaol" should read -- methanol --
Col. 7, line 52; "etheral" should read -- ethereal --

Col. 8, line 16; "NMR(CDCl$^3$)$\delta$:2.97(N+--CH$_3$)" should read

-- NMR(CDCl$_3$)$\delta$:2.97(N+ - CH$_3$) --

Col. 8, line 39, under Col. heading "H"; "6.20" should read -- 7.20 --
Col. 11, line 52; "Elemental Analysis: $C_{19}H_{24}BrNS_2$" delete entire line.
Col. 12, line 22; "ehtyl" should read -- ethyl --
Col. 12, line 40; "obtaned" should read -- obtained --

UNITED STATES PATENT AND TRADEMARK OFFICE
CERTIFICATE OF CORRECTION

PATENT NO. : 4,205,074
DATED : May 27, 1980
INVENTOR(S) : Hideo Kato and Eiichi Koshinaka It is certified that error appears in the above—identified patent and that said Letters Patent is hereby corrected as shown below:

Col. 15, line 13; "1-(Diphenylmethyleneindolizidine" should read with the -- ( -- deleted.
Col. 16, line 24; "hydroxymethy]" should read -- hydroxymethyl] --
Col. 16, line 48; "metling" should read -- melting --
Col. 19, line 10; "diastereoisomers." should read -- diastereoisomers.' --
Col. 19, line 19; "176°-77°" should read -- 176°-177° --
Col. 19, Example 46, col. headed "Physical Data", line 3 of Example; delete "(decompd.)"
Col. 19, Example 47, col. headed "Compound", line 1 of Example; "3-[m.p. 286°-288°C." should read -- 3-[1,1-(Dithien-2-yl)-1-hydroxy- --
Col. 19, Example 47, col. headed "Physical Data", line 1 of Example is left blank but should read -- m.p. 286-288°C. --
Col. 19, Example 47, col. headed "Compound", line 2 of Example; "methyl](3)" should read -- methyl](e) --
Col. 20, line 16; "and quaternary" should read -- and a quaternary --

UNITED STATES PATENT AND TRADEMARK OFFICE
CERTIFICATE OF CORRECTION

PATENT NO. : 4,205,074

DATED : May 27, 1980

INVENTOR(S) : Hideo Kato and Eiichi Koshinaka

It is certified that error appears in the above—identified patent and that said Letters Patent is hereby corrected as shown below:

Col. 4, line 22; "carrers" should read -- carriers --
Col. 4, line 31; "may" should read -- many --
Col. 5, line 12; "nit" should read -- unit --
Col. 15, line 33; "gl" should read -- gm --
Col. 17, line 5; "hydrochlori" should read -- hydrochloric --
Col. 18, line 22; "nOhexane" should read -- n-hexane --

Signed and Sealed this

Seventeenth Day of February 1981

[SEAL]

Attest:

RENE D. TEGTMEYER

Attesting Officer

Acting Commissioner of Patents and Trademarks